United States Patent [19]

Rabinowitz

[11] Patent Number: 5,064,762

[45] Date of Patent: Nov. 12, 1991

[54] INCREASING THE INOSITOL YIELD FROM ALMOND HULLS

[76] Inventor: Israel N. Rabinowitz, 2534 Foothill Rd., Santa Barbara, Calif. 93105

[21] Appl. No.: 630,429

[22] Filed: Dec. 19, 1990

Related U.S. Application Data

[63] Continuation of Ser. No. 47,884, May 7, 1987, abandoned.

[51] Int. Cl.[5] ................................................ C12P 1/02
[52] U.S. Cl. ...................................... 435/155; 435/942
[58] Field of Search ................................ 435/155, 942

[56] References Cited

U.S. PATENT DOCUMENTS 4,482,761 11/1984 Chao et al. ............................ 568/833

FOREIGN PATENT DOCUMENTS 0808128 1/1959 United Kingdom ................ 435/942

OTHER PUBLICATIONS

Sequeira et al., "The Carbohydrate Compsition of Almond Hulls" J Agr Food Chem 18(5): 950–951, 1970.
Greenberg et al., "Regulatory Mutations of Inositol Biosynthesis in Yeast: Isolation of Inositol-Excreting Mutants" *Genetics 100: 19–33, Jan. 1982.*

*Primary Examiner*—Douglas W. Robinson
*Assistant Examiner*—Jean C. Witz
*Attorney, Agent, or Firm*—Donald D. Mon

[57] ABSTRACT

This invention relates to the extraction of useful products from almond hulls, and more specifically to increasing the yield of myo-inositol from almond hulls.

2 Claims, No Drawings

INCREASING THE INOSITOL YIELD FROM ALMOND HULLS

BACKGROUND OF THE INVENTION

The chemical composition of almond hulls has been the source of previous comment in the literature. For example, in U.S. Pat. No. 4,482,761 to Chao there is disclosed the presence of myo-inositol and other sugar alcohols, and of sugars, in almond hulls. The water extract of almond hulls is disclosed. It is sometimes referred to herein as "almond fruit syrup". In this patent, the use of molecular sieves to seperate these useful compounds from the water extract is also disclosed. Sequeira et al, "The carbohydrate Composition of Almond Hulls", J. Agri. Food Chem. Vol. 18 (1970) pp. 950-951 provides another discussion of the compostion of almond hulls.

Almond hulls are a natural product forming a part of the almond fruit itself. They are produced as a by-product of the process of producing the most- utilized part of the almond fruit, namely the stone.

It is not a matter of common knowledge, nor well understood in industry and commerce, that the source of the almond nut is a fruit tree. The sweet almond (Prunus amygdalus, or Amygdalus communis) is specifically a stone fruit (drupe), in which the fleshy part, the mesocarp or "hull", is drived from the ovary of the flower and suurounds the shell (endocarp), teguement (thin papery covering ), and finally the stone or "nut" itself. Almond trees are currently cultivated commercially solely for the value of the edible nut, or in the case of the bitter almond, for the flavoring extracts expressed from the otherwise inedible nut. Almonds are most closely related to other stone fruit, such as peach (*Prunus persica*), apricot (*P. armeniaca*) and plum (*P. domestica, P. instititia, et al.*) in which the stone is indeed a stone in the common understanding and is not edible, whereas the mesocarp (not referred to as a "hull") is, and it forms the basis for the commercial exploitation of this fruit.

The process of growth, maturation, abcission, and senescense of the almond fruit, is such that early in its growth stage the "hull" can be eaten by humans, when it possesses pleasing taste, texture, and nutritional value. By maturation and thereafter, the hull is leathery in texture and astringent to the taste, although its nutritional value has actually increased. Unfortunately this increase in nutritional values is accompanied by the presence of other chemical components which can temporarily sicken a human.

As recently as thirty years ago, the nutritional value of the almond hull was not sufficiently understood, and after harvest of the nuts, in California, the hulls were either used for landfill, burned for removal, or sometimes burned for their fuel value. Starting about thirty years ago, agricultural scientists in California introduced and pioneered the use of almond hulls in animal feed, primarily cattle, in which animals the chemical components troublesome to humans do not upset the animals, and nutritional value is obtained at low cost.

The inventor in this instant patent application has observed that several chemical components of almond hulls, present after fruit maturation, have individual and important commercial values, and has devised commercial processes to separate and purify them, leaving very little to waste. For example, prior to the introduction of the use of hulls for animal feed, almond hulls had negative or zero commercial value. Currently, for feed usage, almond hulls have a value averaging about $50/ton. The process invention described herein can raise the value of the almond hull (as separate components) to approximately $800/ton. However, this increased recovery depends heavily on deriving as much as possible of high-value products, and on wasting as little as possible of any part of the starting material.

In this invention the starting material is almond hulls, and the product which at the present time commands a high price and enjoys an elastic demand, is inositol. It is an object of this invention to increase the yield of inositol from almond hulls. Fortuitously, the trade-off is a reduction in products of much lesser value, sometimes with no such reduction at all. For example, some other valuable products (which are not the subject of this invention) such as recoverable vegetable fiber, are not appreciably decreased, if they are decreased at all.

BRIEF DESCRIPTION OF THE INVENTION

Almond hulls which have been kept dry after the fruit has been recovered from the tree, are dry and leathery. They contain inositol, (generally as myo-inositol), sugars, other sugar alcohols, and some precursors of inositol. These hulls also contain naturally-occurring, wild strains of fungi (including yeasts) and bacteria in the spore state, which, when activated by water, excrete enzymes onto the almond hull substrate, that break down certain precursors of inositol and release myo-inositol. This increases the inositol content of the hulls. Even more, these strains germinate and increase their cell mass during the process. Their cells also contain recoverable inositol. Thus, an augmented increase is attained- both as the result of excretion and of cell-mass growth- an action on the substrate hulls, and an internal cellular production.

Of course this procedure must be terminated before succeeding processes begin significantly to consume inositol as a carbon source for growth, and an essential nutrient for growth.

From the foregoing it will be evident that there are three useful techniques to increase inositol production, using any yeast system that excretes inositol or enzymes which will do so. They are as follows:
1. The dry hulls may be wetted and incubated at an appropriate temperature and for a suitable period of time.
2. Surface culture of the yeast on a suitable growth medium, such as on almond fruit syrup.
3. Submerged culture of the yeast in a suitable growth medium such as almond fruit syrup.

In all of the above cases, the naturally occurring strains can be utilized. However, important improvements can be attained by utilizing strains which have been specifically identified as organisms which can grow on sugary media and excrete inositol. The use of such single or substantially pure monoculture growth of organisms on the hulls or in the syrup has substantial advantages. This has the capacity to improve the yield of myoinositol for the following reasons: (I) among the known yeast genera capable of excreting enzymes which produce inositol from inositol phosphates in the almond fruit is Cryptococcus. Cryptococcus however, differs from other identified genera and species in also having the capability of utilizing inositol as a carbon source for growth. It would obviously be advantageous to limit the growth of this yeast as it could consume as much or more inositol, than it produces. (II) Substantially pure monoculture would most effectively utilize the "biosphere" or growing area available to the productive microbe, as it would not have to compete for growing space and available nutrients with less productive, or indeed deleterious organisms. (III) Substantially pure monoculture or single strain growth is also more amenable to optimization of growth and production conditions. That is, for a single strain, the parameters of temperature for growth, total water activity, added nutrients and their concentrations, pH, and time between inoculation and harvest, can be fine tuned for maximal production in ways not possible with mixed population growth requiring competing conditions for growth and production.

Throughout both pre-recorded and recorded history, strain election for useful microbes in the production of food and beverage has advanced by selection of naturally occurring newly mutated types. The rate of production of new mutants, their selection, and application, has increased within this last century, using contemporary techniques for mutation and selection. Often, uses for new mutants are not recognized at the time of their creation, either because all of the properties of the mutant have not been discovered, or because the mutants were created for different purposes. This latter case was true for the creation of a Saccharomyces cerevisae mutant which overproduces and excretes myo-inositol (M. L. Greenberg, B. Reiner, S. A. Henry, Genetics 100 19-33, 1982); (M. L. Greenberg, P. Goldwasser, S. A. Henry, Mol. Gen. Genet. 186, 157-163, 1982). This mutant was created pursuant to basic research into mechanisms of gene expression of the control of production and utilization of an essential nutrient (myo-inositol) in eukaryotic organisms (including yeast and man). This yeast is the preferred strain for use in this invention. It was not the intent to produce an organism which would synthesize a commercially valuable material. At the time of the creation of the mutant, there was only one viable industrial process for the production of myo-inositol, and this depended upon manufacturing of myoinositol from a phosphate precursor. There were no known commercial techniques in 1982 for the extraction of myo-inositol itself from a material and its subsequent utilization by various end users. Commonly performed laboratory extractions of myoinositol would result in prohibitive market costs if attempted on a commercial scale.

A commercial process for extraction, purification and concentration of myo-inositol from almond fruit, along with extraction of other valuable materials utilizing molecular sieve techniques is favorable, with respect to myo-inositol, if its starting concentration at process inception is approximately 3%-4%. Economic viability increases substantially for each incremental percentage point of starting concentration. The major reason for the economic viability of the almond fruit process is recovery of several products simultaneously, with very little wastage of starting feedstock. In this regard, utilization of an inositol excreting yeast in the process has startling effects on process economic viability. All of the products previously recoverable remain so, and with no increase in process feedstock (almond fruit) the yield of recoverable inositol increases significantly, with attendant increase in process profitability. In fact, with proper control of growth conditions, and time of harvest, several other products increase in total concentration, notably the sugars glucose and fructose, and the sugar alcohol myo-inositol.

Use of a (substantially) monoculture of the inositol excreting *S. cerevisiae* strain can produce at least an equal amount of additional inositol as does the mixed wild strains, by a different mechanism, and has the potential of increasing the yield of myo-inositol several fold. Again, this increase can be achieved by using almond fruit or almond fruit syrup as growth medium, thereby forming a continuously replenishable growth medium, which is finally utilized for products, and recovery of spent yeast for product value also, most commonly animal feed.

DETAILED DESCRIPTION OF THE INVENTION

A master stock of frozen or otherwise processed inositol excreting spores will be kept, and a production of "working" stock germinated yeast will be periodically assayed for excretion activity compared to master stock progeny.

Working stock spores can be activated for production in at least three different modes:

Mode I. Spores are sprayed onto almond fruit (hulls) with "preincubation" water. It will usually not be necessary to sterilize the fruit prior to introduction of the spores, although under certain circumstances it may be preferable to do so, e.g. in usage of rain damaged fruit where wild yeast growth may have achieved very high density. Normally, careful attention to collection and storage will be sufficient to insure preferential growth of the applied spores over that of the natural yeast spore population, and resident bacterial populations. This is assisted by keeping the hulls dry until they are ready to be processed. Working spores may also be germinated through a series of work up steps in different growth media of increasing volume, procedures well known to the art. The germinated and actively vegetating yeasts can then be sprayed onto the almond fruit, as intact organisms, or partially disintegrated organisms, with intact, active hyphae. In both of these options "preincubation" water may have salts (e.g. nitrates, phosphates) and other beneficial additives added to the water; the pH of the water may be altered and buffered, and the total water activity closely controlled. These steps may be necessary under certain conditions of feedstock (fruit) conditions, process water quality, and ambient temperature. These steps will aid in growth of the substantially monoculture of inositol excreting yeast and depress growth of wild types of fungi and bacteria. Aeration of growth will also be closely controlled. This can be achieved through a number of mechanisms, including, for example, a "cement mixer" type of tumbler, with aeration pores in its walls. This can be recognized as a simple scale up design from commonly used laboratory tumbler-aerators.

Mode II. Working spores, or partially germinated yeast, or hyphae, are grown in surface culture on almond fruit extract or syrup. Surface culture of microbes is recognized as a "traditional" method of recovering secondary metabolites of commercial value from various microbes. In application to almond fruit extract however there are at least two significant differences:

a. Normally, a typical growth substrate, such as cane or beet molasses or corn steep liquor, must first be considerably diluted with water in order to obtain proper sugars and nutrient concentration, proper osmotic strength and viscosity, proper pH, and usually further treatment to remove potentially toxic materials such as heavy metals. An almond fruit syrup that is derived from counter-current water extraction of almond fruit, is almost perfect the above conditions to support yeast growth. The extract need not even be coarse filtered to remove suspended solids, but it may be, in order to facilitate cleaning and sanitation of the surface culture vessels. This almond fruit extract has been repeatedly shown to be an excellent growth media for yeasts by this inventor, but again slight modifications of pH and adjustment of ambient temperature may be made to effect optimal growth and production.

b. Also unlike "traditional" surface culture methodology, the growth media in this application, almond fruit syrup, is not discarded after use, but remains in the process stream for further treatment and recovery of valuable products. The inositol excreted by the yeast becomes a part of the almond syrup fluid, which is then concentrated prior to separation of the syrup in to its valuable components such as organic acids and glucose-frutose sweetener syrup, and inositol solids. The removal of yeast growth from the syrup is effected by conventional means such as centrifugation, filter press, and/or ultrafiltration.

Mode III. A third mode of application of working inositol excreting yeasts is the submerged culture of yeast in production scale fermentors. Growth media in the fermentor is the almond fruit syrup. This class of biological processing is gaining increasing favor in industry as the consequence of rapid improvements in fermentor design and attendant cost efficiency.

This submerged culture mode of operation may ultimately become the mode of choice. The principles of submerged culture operation are well known, but it is also well known that this process is the least "forgiving" of the procedures which may be employed, in that each system of microbe/growth medium will have its individual, distinct problems which must be solved. For this reason, submerged growth fermentor methodology will be gradually worked into the almond fruit plant processing strain at a cautious pace, if the cost effectiveness of such a step continues to be potentially attractive, in actual plant operations.

In all three of the application modes described, the inositol excreting yeast resides for a time at selected points in an established process stream and contributes a significant increment in one product's production (inositol) without unduly reducing any other product's recovery, and adding negligible, if any, energy costs to the process system, and negligible feedstock (spores) and wastage mass (spent yeast) to the system.

All of the foregoing processes may be accomplished with the use only of the naturally occurring strains which exist on the fruit when it is harvested, instead of adding specific yeasts. The use of specific yeast does improve the predictability of the inositol concentration, because the type of wild strain and its behavior of the wild material is uncertain. It is not necessary to sterilize the hulls, although that could be done to remove the wild strains. Simpler practice is merely to overcome them by adding an excess of specific strains which will overwhelm the natural strains.

Thus, this invention contemplates the attentive harvest of the hulls, protecting them against being wetted while in the orchard, and keeping them dry during storage, until just before they are to be used. Then any of the disclosed three modes may be used to increase the inositol concentration, employing either the natural strains already present, or adding specific yeast which has the demonstrated capacity to increase the inositol content.

When the maximum inositol content is attained, or for that matter, some increased concentration having in mind other parameters of the system which might dictate attaining less than the maximum inositol concentration, the inositol and yeasts will be separated from one another. One technique is to remove the inositol, leaving the yeast in the growth medium. Preferably the solids will be separated, if they have not been removed already, and the yeasts will be removed from the syrup, by filtration, centrifugation, or otherwise.

The inositol may be removed by means such as taught in the Chao patent, and the remainder of the almond hull and syrup may be used for various purposes which are not the subject of this invention.

This invention thereby profoundly improves the production of inositol from almond hulls, and importantly increases the value of the hulls themselves and of the products derived from them.

This invention is not to be limited by the embodiments described in the specification, which are given by way of example and not of limitation, but only in accordance with the scope of the appended claims.

I claim:

1. A process for increasing the amount of myoinositol obtainable from almond hulls, said almond hulls not having been wet with water since their harvest to the extent which would activate naturally-occurring strains of fungi on and in said almond hulls; said method comprising the following:
   (a) wetting said hulls with water in an amount to activate said naturally-occurring fungi carried by said almond hulls as a consequence of the almond hull's growth on the almond tree and residence time on the orchard floor, and incubating said almond hulls while thus wetted for a time sufficient to permit the mass of said naturally-occurring fungi to increase, and for the amount of myo-inositol to be increased as a consequence of the growth of these fungi; and
   (b) after an increase in the concentration of myo-inositol is developed, submerging said almond hulls in water to dissolve sugar and sugar alcohols from said almond hulls thereby to form an almond fruit syrup containing said myo-inositol; and
   (c) removing almond hull residue from said almond fruit syrup.

2. A process for increasing the amount of myo-inositol obtainable from harvested almond hulls, said almond hulls not having been wet with water since their harvest to the extent which would activate naturally-occurring strains of fungi on and in said almond hulls, said method comprising the following steps:
   (a) submerging said almond hulls in water to dissolve sugars and sugar alcohols from said almond hulls, thereby to form an almond fruit syrup containing myo-inositol present in said almond hulls and also to contain naturally-occurring strains of fungi which exist in almond hulls as a consequence of the almond hull's growth on the almond tree and residence on the orchard floor, whose effect is the increase the concentration of myoinositol; and
   (b) encouraging the growth of said fungi strains throughout said syrup to increase the amount of myo-inositol therein.

* * * * *